United States Patent [19]

Harris

[11] Patent Number: 4,715,380

[45] Date of Patent: Dec. 29, 1987

[54] CAPPED PACER NECK CONTAINING A CONNECTOR ASSEMBLY

[75] Inventor: Donald L. Harris, Key Largo, Fla.

[73] Assignee: Telectronics N.V., Curacao, Netherlands Antilles

[21] Appl. No.: 848,026

[22] Filed: Apr. 3, 1986

[51] Int. Cl.[4] ................. A61N 1/00; H01R 11/00
[52] U.S. Cl. .................. 128/419 P; 128/784; 29/883; 439/592; 439/271; 439/587
[58] Field of Search ............ 339/61 R, 61 M, 94, 339/59-60; 128/419 P, 419 PG, 784, 786, 639-644; 29/883, 876

[56] References Cited

U.S. PATENT DOCUMENTS

| | | | |
|---|---|---|---|
| 3,271,727 | 9/1966 | Nelson | 339/94 M |
| 3,760,332 | 9/1973 | Berkovits et al. | 339/66 R |
| 3,908,668 | 9/1975 | Bolduc | 128/419 P |
| 4,112,953 | 9/1978 | Shanker et al. | 128/419 P |
| 4,141,752 | 2/1979 | Shipko | 128/419 P |
| 4,142,532 | 3/1979 | Ware | 128/419 P |
| 4,152,540 | 5/1979 | Duncan et al. | 174/152 GM |
| 4,154,248 | 5/1979 | Jones | 128/419 P |
| 4,182,345 | 1/1980 | Grose | 128/419 P |
| 4,226,244 | 10/1980 | Coury et al. | 128/419 P |
| 4,236,525 | 12/1980 | Sluetz et al. | 128/419 P |
| 4,262,982 | 4/1981 | Kenny | 339/60 R |
| 4,301,805 | 11/1981 | Peers-Trevarton et al. | 128/419 P |
| 4,445,511 | 5/1984 | Cowdery et al. | 128/419 P |
| 4,488,557 | 12/1984 | Engel | 128/640 |
| 4,583,543 | 4/1986 | Peers-Trevarton | 128/419 P |
| 4,628,934 | 12/1986 | Pohndorf et al. | 128/419 PG |

*Primary Examiner*—John McQuade
*Assistant Examiner*—Paula A. Austin
*Attorney, Agent, or Firm*—Henry W. Collins; Thomas R. Vigil

[57] ABSTRACT

The cardiac pacing system comprises a cardiac pacer, and a multiconductor pacing lead having a distal end and a proximal end having a plurality of spaced apart ring electrodes thereon. The pacer comprises a metal case mounting electronic/electrical circuitry, and a power supply therein and having a top side. A soft pliable elongate neck is mounted to the top side of the case. A connector assembly is located inside said neck for connecting the cardiac pacer with the proximal end of the pacing lead and comprises a plurality of spaced-apart U-shaped electrical contacts and insulated conductors extending through the top side for coupling the electrical contacts to electrical circuitry in the case. The neck has at least one elongate lumen therein into which extend the electrical contacts and has an open end for receiving the proximal end of the pacing lead. A hard elongate cap which is sized to fit over at least a portion of the neck containing the electrical contacts, is releasably fixed over the neck and has a smaller width than the width of the neck so that after the proximal end of the lead is inserted into the lumen, fixing of the cap over the neck will compress the electrical contacts against the ring electrodes.

25 Claims, 8 Drawing Figures

CAPPED PACER NECK CONTAINING A CONNECTOR ASSEMBLY

BACKGROUND OF THE INVENTION

1. Field of the Invention

The present invention relates to connector assemblies for cardiac pacing leads, and more particularly to a connector assembly which readily connects to the proximal end of an in-line multielectrode pacing lead. The connector assembly is designed to be expandable to accommodate a plurality of electrical contacts for making contact with ring electrodes on the proximal end of the pacing lead and is mounted in a soft, pliable, so-called pacer neck, which fits closely about the pacing lead to prevent fluid flow into the connector assembly and between the electrical contacts and includes a cap which fits tightly over the neck so as to squeeze the contacts against the ring electrodes on the pacing lead.

2. Description of the Prior Art

Pacing systems include a pacer, which comprises a metal container or case which contains electronic circuitry and a power supply, and a pacing lead. The proximal end of the lead is connected to output terminals of the pacer in a component of the pacer which is commonly referred to as the neck of the pacer mounted to a top side of the case.

Multiple electrode cardiac pacing leads are well known and have been utilized for pacing both the atrial and ventricular chambers of the heart. Such a pacing lead includes a multipolar electrode assembly at the distal end and terminal ring electrodes or bands at the proximal end. The multipolar electrodes at the distal end of the lead usually comprise a tip electrode and one or more ring electrodes along the length of the lead. Additionally, the lead may contain one or more sensors along its length which measure and monitor physiological parmeters, such as the partial pressure of oxygen or carbon dioxide within the chambers of the heart.

In a pacing system with one electrode on the pacing lead, the distal end of the lead contains the electrode and is usually placed in the ventricle of the heart. The electrode is connected to the lead by an insulated helically coiled wire conductor. At the proximal end of the lead, a terminal pin is affixed to the lead. This pin is inserted into the pacer neck where it makes contact with a pacer lead connector socket which is, in turn, connected to cardiac pacer circuitry and a power source in the pacer case.

With one electrode on the distal end of the lead, referred to as a unipolar system, one pacer lead connector or contact is needed in the neck of the pacer to serve as a cathode connector, with the case or can of the pacer normally serving as an anode. In a bipolar system, where two electrodes are on the distal end of the lead, a pacing lead terminal pin and a terminal ring electrode or band are provided on the proximal end of the lead and two pacer lead connectors or contacts are necessary in the neck of the pacer.

Currently, cardiac pacing systems focus upon (a) the sensing of electrical signals generated by the myocardium or middle layer of the atrial and/or ventricular chambers of the heart and (b) the stimulation of one or both of these chambers in the absence of spontaneous electrical activity. In such a dual system, either two different leads are used or the lead used measures ventricular activity at its tip and atrial activity along its length and therefore, more than one connector is needed in the pacer neck. In dual chamber unipolar systems, two pacer lead connectors are required in the neck of the pacer; one for the atrial lead terminal ring electrode and one for the ventricular lead terminal pin. In a bipolar dual chamber system, four pacer lead connectors are required in the pacer neck for connection to the pacing lead proximal terminal pin and terminal ring electrodes for monitoring both chambers of the heart.

Future pacing systems will include physiological sensors, either as part of the pacing lead or separate from it. These physiological sensors will measure parameters such as oxygen and carbon dioxide levels, pH or any combination thereof, to name a few. These parameters will be transmitted to the pacer circuitry for use in setting various pacer outputs. Additionally, each of these sensors will require an electrical contact or connector within the pacer neck in addition to the contacts or connectors described above for connection to the electrodes for sensing electrical activity.

Multielectrode pacing leads most suitable for this type of electrode and sensor system include a lead with multiple ring electrodes and sensors on the distal end and multiple terminal ring electrodes on the proximal end of the lead in an in-line arrangement. Such a lead allows the monitoring of several different parameters while only causing one insertion to be made into the heart which reduces trauma. An example of such a lead is disclosed in U.S. Pat. No. 4,469,104 which discloses a lead assembly for a body implantable tissue stimulator which contains a connector system of a terminal electrode assembly on the proximal end of the lead and a connector assembly in the pacer neck which relies on garter springs or conductive elastic O-rings to contact each, in-line ring electrode on the proximal end of the lead. Although such a connector system is effective, the terminal assembly on the proximal end of the lead electrode is hard to manufacture, is sometimes difficult to insert into the pacer neck and is too large to accommodate a large number of terminal ring electrodes within the minute confines of the pacer neck.

Heretofore various connectors have been utilized for connecting the proximal end of a single or multielectrode pacing lead to the electrical output terminals in the neck of a pacer. The most commmon type of connector system employs a terminal pin on the proximal end of the pacing lead which is secured inside the the neck to a connector of the pacer by a set screw. This arrangement is not completely desirable since it usually requires the surgeon to tighten the screw after the terminal pin of the lead is in place inside the neck of the pacer during implantation in a body. Such a procedure is complicated due to the small size of the screw and the conditions of the operating room.

Additionally, the number of contacts for a multielectrode lead is restricted if a different set screw is needed for each lead terminal ring electrode received within the connector assembly. Present connectors which employ such a set screw are limited to a maximum of four connectors due to the size limitations of the pacer neck.

Finally, the set screws encounter problems with body fluids over an extended period of time which causes deterioration of the screw and entry of fluid into the electrical contact area causing damage and malfunction. In some instances, a cap has been used to cover each screw head but such a design has not been entirely effective and has further complicated the installation procedure.

Therefore, the need exists for a multiple contact connector assembly in a pacer neck which is small in size, easy to manufacture, readily accommodates a multielectrode lead, is impervious to body fluid and can be adapted to receive and make contact with a number of ring electrodes on the lead, the number being variable and dependent upon the number of distal electodes and sensors required for a particular patient.

As will be described in greater detail hereinafter, the assembly of the present invention provides a device which is capable of readily accommodating an in-line multielectrode lead without any complex installation procedures and which is completed sealed from the body it is implanted in.

Moreover, the connector assembly of the present invention differs from the previously proposed connector assemblies and pacer neck constructions by providing a connector assembly and pacer neck construction which is small in size, contains strain relief for the lead, is easy to use, can accommodate a large number of electrode contacts, provides for pressure against the contacts engaging ring electrodes on a pacing lead, is easy to manufacture, and maintains high reliability of electrical contact throughout the life of the pacing system.

SUMMARY OF THE INVENTION

According to the present invention there is provided a cardiac pacing system comprising a cardiac pacer and a pacing lead. The pacing lead has a distal end and a proximal end with at least one ring electrode on the proximal end. The pacer comprises a metal case mounting electronic/electrical circuitry and a power supply therein and having a top side. A soft pliable elongate neck is mounted to the top side of the case. A connector assembly is located inside the neck for connecting the cardiac pacer with the proximal end of the pacing lead. The connector assembly comprises at least one generally U-shaped electrical contact, and an insulated conductor extending through the top side for coupling the at least one electrical contact to electrical circuitry in the case. The neck has at least one elongate lumen therein into which extends the at least one electrical contact and which has an open end for receiving the proximal end of the pacing lead. A hard elongate cap is sized to fit over at least a portion of the neck containing the at least one electrical contact, is releasably fixed over the neck, and has a smaller width than the width of the neck so that after the proximal end of the lead is inserted into the lumen, fixing of the cap over the neck will compress the at least one electrical contact against the at least one ring electrode.

Further according to the invention there is provided a method of connecting the proximal end of an implantable cardiac pacing lead to at least one electrical contact within a pacer neck of a cardiac pacer. The method comprises the steps of: providing at least one flexible, electrical, U-shaped, spring contact having spaced apart legs on top of the metal case of a cardiac pacer; molding a soft, pliable elastomeric neck about the spring contact and simultaneously forming a lumen in the neck which is in communication with the spring contact, or has a portion of the spring contact disposed therein, inserting the proximal end portion of a pacing lead which has at least one ring electrode thereon into the lumen until the end thereof bottoms against the closed end of the lumen; constructing and arranging the ring electrode and the spring contact so that when the proximal end of the lead bottoms against the closed end of the lumen, the ring electrode is in registry with and between the legs of the spring contact; and causing the spring contact to be compressed against the ring electrode by fixing a hard cap, having an inside width less than the width of the neck, over the neck to the metal case.

DESCRIPTION OF THE PREFERRED EMBODIMENT

Figure 1:
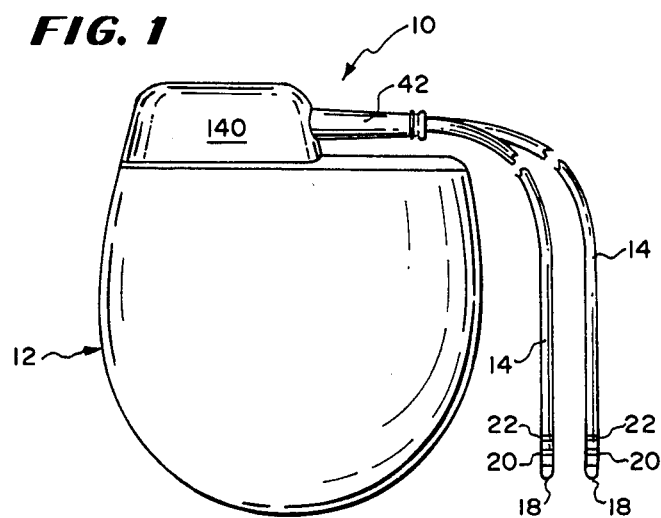
FIG. 1 is a side plan view of a cardiac pacing system constructed according to the teachings of the present invention.

Referring now to the drawings in greater detail, there is illustrated in FIG. 1 a cardiac pacing assembly 10 which comprises a cardiac pacer 12 constructed according to the teachings of the present invention, and first and second identical cardiac pacing leads 14.

Figure 7:
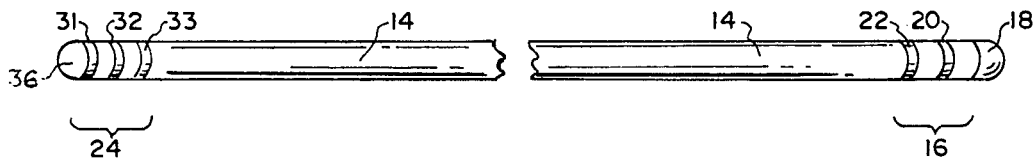
FIG. 7 is a perspective view of the distal and proximal ends of one of the pacing leads of the pacing system shown in FIG. 1.

As best shown in FIG. 7 each of the cardiac pacing leads 14 has a distal end portion 16 with a tip electrode 18 at the end thereof and, spaced rearwardly thereof, at least two ring electrodes 20 and 22.

The lead 14 has a proximal end portion 24 in which are mounted at least three ring electrodes 31, 32 and 33 which are spaced from one another. The proximal electrode 31 is spaced from a proximal end 36 of the lead 14. The proximal end portion 24 is adapted to be mounted in a neck 40 (FIGS. 2 and 3) of the pacer 12.

Figure 3:
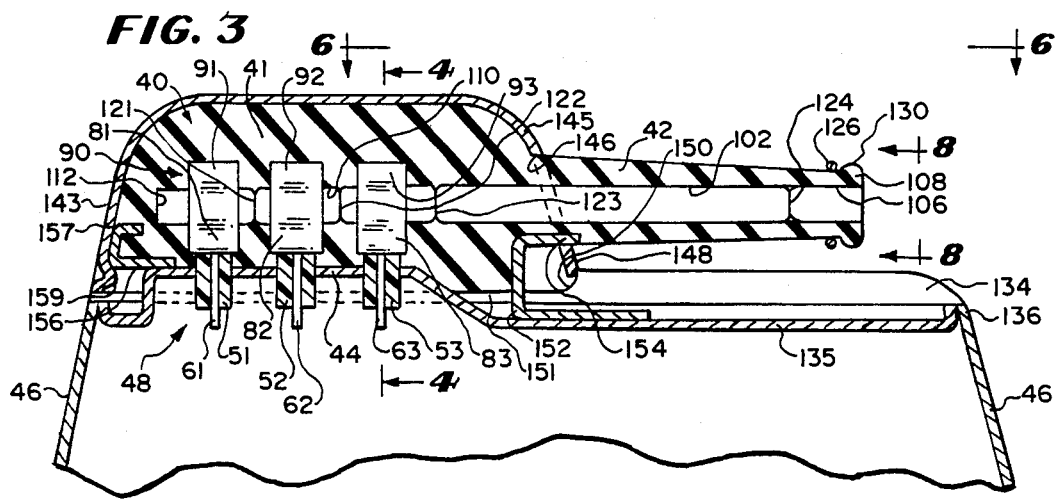
FIG. 3 is an enlarged vertical sectional view of the pacer neck, the cap and a fragmentary portion of the upper portion of the metal case of the pacer, shown in FIG. 1.

As best shown in FIG. 3, the pacer neck 40 has a main body portion 41 and a snout portion 42 and is made of an elastomeric material, such as polyurethane silicone or a Silastic TM material. The soft, pliable elastomeric neck 40 is mounted on an offset top side portion 44 of a metal case 46 of the pacer 12 in which are contained electronic/electrical circuitry and a power supply (not shown).

Extending through the top side portion 44 of the metal case 46 is a first plurality 48 of insulated feed throughs 51, 52 and 53, each having a wire conductor 61, 62 and 63 extending therethrough. Typically, the upper end of each wire conductor 61, 62 or 63 is welded to a lower bight portion 81, 82 or 83 of one of a plurality 90 of electrical, U-shaped spring contacts 91, 92 or 93.

Figure 4:
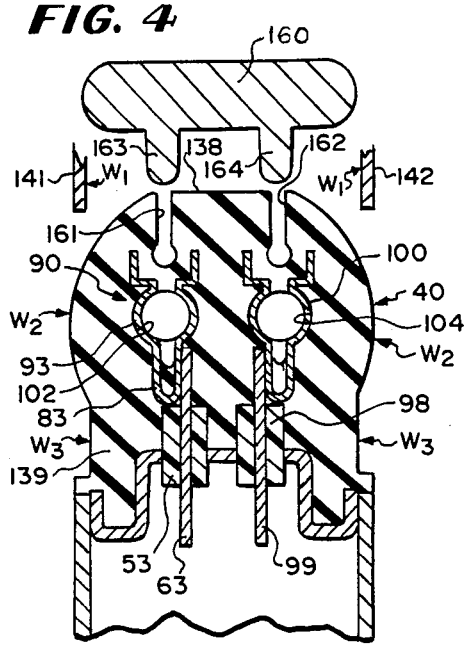
FIG. 4 is a vertical sectional view through a main body portion of the pacer neck with the cap of the pacer in a raised position and is taken along line 4—4 of FIG. 3.

As shown in FIG. 4, another plurality of feedthroughs 98, of wire conductors 99, and of electrical U-shaped, spring contacts 100 are mounted on the top side portion 44 of the case 46 and extend into the main body portion 41 of the neck 40. Only one insulated feedthrough 98, one wire connector 99 and one spring contact 100 are shown in FIG. 4.

It will be understood that in this embodiment there are two pluralities of contacts 90 and 100, each comprising three contacts which are spaced apart along the length of the main body portion 41 of the elongate neck 40 and which are situated adjacent each other but insulated from each other by the elastomeric neck 40 molded therearound.

When the neck 40 is molded around the electrical contacts 91, 92, 93 and 100 on the top side portion 44 of the case 46, first and second lumens 102 and 104 are formed in the neck 40 as shown in FIGS. 3 and 4. These lumens 102 and 104 are essentially identical and only the first lumen 102 will be described in detail with reference to FIG. 3.

Referring now to FIG. 3, it will be seen that the lumen 102 has an open end 106 at an outer end 108 of the snout portion 42 and extends through the snout portion 42 to a main portion 110 that is located within the main body portion 41. Then an inner end 112 of the lumen 102 is closed.

This lumen 102 is adapted to receive the proximal end portion 24 of the lead 14 shown in FIG. 7 and the distance between the proximal end 36 of lead 14 and the ring electrode 31 thereon is equal to the distance between the closed inner end 112 of the lumen inner end 102 and the electrical contact 91 so that once the proximal end 36 of the lead 14 is inserted into the lumen 102 and bottoms on the closed lumen inner end 112, the ring electrodes 31, 32 and 33 will be in registry with the contacts 91, 92 and 93.

To provide for sealing between the contacts 91, 92 and 93 thereby to prevent electrolytic fluids from communicating between the contacts 91, 92 and 93 after the proximal end portion 24 of the pacing lead 14 is inserted in the lumen 102, three annular ribs 121, 122 and 123 are formed in the cylindrical wall of the lumen 102, as shown in FIG. 3. Preferably to further assist in the prevention of entry of electrolytic fluids into the lumen 102, an additional annular rib 124 is formed within the lumen 102 in the snout portion 42 adjacent the outer end 108 of the snout portion 42.

Figure 6:
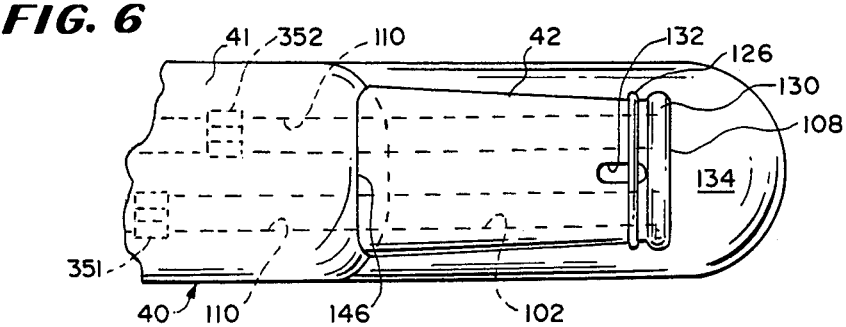
FIG. 6 is a fragmentary top plan view of a portion of the pacer viewing same from the top and is taken along line 6—6 of FIG. 3.
Figure 8:
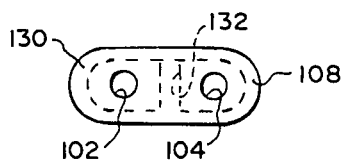
FIG. 8 is an end view of a snout portion of the pacer neck and is taken along line 8—8 of FIG. 1.

To facilitate the tying of a suture 126 about the outer end 108 of the snout portion 42, the snout portion 42 is flared to form a bead 130 as shown in FIGS. 3, 6 and 8. The suture 126 is tied around the snout portion 42 right behind the bead 130.

Further, and as best shown in FIG. 6, to facilitate the tying of suture 126 around the outer end 108 of the snout portion 42 and around each of the lumens 102 and 104, an opening 132 is provided in the snout portion 42 between the lumens 102 and 104 so that a portion of the suture 126 can extend through the opening 132 and around the lumen 102 and another portion of the suture 126 can also extend through the opening 132 but around the other lumen 104.

Also, it will be appreciated from FIG. 8 that the snout portion 42 is generally oval in cross-section and as shown in FIG. 3 is positioned over an elastomeric covering 134 on another top side portion 135 of the case 46.

The elastomeric covering 134 extends to a corner 136 of the case 46 adjacent one side 137 of the case 46.

Further in accordance with the teachings of the present invention, an elongate hard cap or cover 140, which can be made of hard plastic and which is preferably made of metal, is mounted over the main body portion 41 of the neck 40. The cap 140 is configured to have substantially the same shape as the main body portion 41 but has an inside width $W_1$, (FIG. 4) which is less than the largest width $W_2$ of the main body portion 41 of the neck 40.

As shown, the main body portion 41, in cross-section, is rounded on opposite sides from a top surface 138 to a narrower width portion 139 having a width $W_3$, the rounded side having the largest width $W_2$.

The slots 161 and 162 and the lumens 102 and 104 accomodate displaced material of the neck which are displaced by the squeezed in portions of the rounded sides of the main body portion 41 when the cover 140 is forced over the main body portion 41.

As shown in FIG. 4, the cap 140 has side walls 141 and 142 and as shown in FIG. 3 has an end wall 143 above one end edge 144 of the pacer case 46 and another end wall 145 having an opening 146 therein through which the snout portion 42 extends.

A lower end edge 148 of the end wall 145 is constructed and arranged to abut a shoulder 150 formed in the elastomeric covering 134. In this respect, it will be noted that a portion 151 of the covering 134 is of reduced thickness below the neck 40, as shown, so as to form the shoulder 150.

Figure 2:
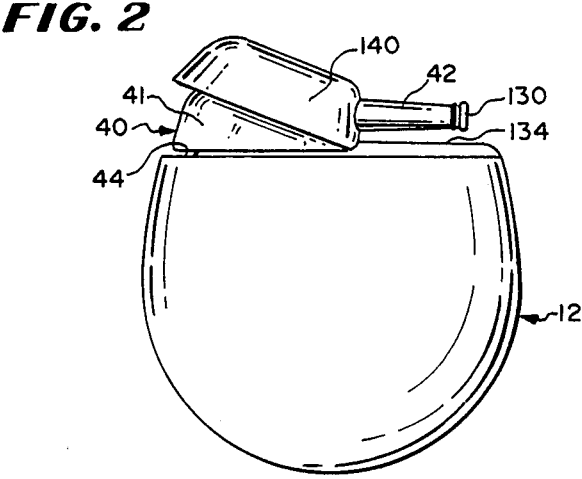
FIG. 2 is a side plan view of the pacer of the pacing system shown in FIG. 1 with a cap of the pacer rotated upwardly about a hinge from a releasably fixed position thereof shown in FIG. 1.

A hinge forming clip 152 is fixed, such as by welding, to the top side portion 135 and extends upwardly through the neck main body portion 41 to a generally horizontally extending flange 154 which extends toward the snout portion 42 and through the opening 146. The flange 154 forms a fulcrum or hinge point about which the cap 140 can be rotated as shown in FIG. 2.

On the other end of the neck main body portion 41, a detent forming clip 156 is fixed, such as by welding, to the top side portion 44 and extends toward the end wall 143 of the cap 140 to a hook or detent formation 157. A crimp is formed in a lower side margin 158 of the end wall 143 so as to form an inwardly extending rib or detent 159 which is snap fittingly received over the detent formation 157 to releasably fix the cap 140 in place over the neck main body portion 41.

The cap 140 is adapted to be rotated about the flange 154 for raising the other end wall 143 of the cap 140 above the top side portion 44 of the case 46 sufficient to raise the side walls 141 and 142 above the electrical contacts 91, 92, 93 and 100 within the neck 40 (FIG. 2) and sufficient to allow insertion of an insertion tool or wedge tool 160 (FIG. 4) beneath the cap 140 and into slots 161 and 162 (FIG. 4) formed in the main body portion 41 of the neck 40. Each of the slots 161 and 162 extends longitudinally along the length of the main body portion 41 of the neck 40 and downwardly into the neck 40 to a point above the respective lumens 102 and 104. Each of these slots 161 and 162 is designed to receive an elongate blade-like rib 163 or 164 of the wedge tool 160 which is adapted to be inserted in the respective slots 161 and 162 and pushed downwardly to spread the U-shaped spring contacts 91, 92, 93 and 100 apart to facilitate insertion or removal of the proximal end portion 24 of the lead 14 into the lumen 102 or 104 and to provide compressive space for the cap 140 to close the contacts 91, 92, 93 and 100 around the lead terminal ring electrodes 31, 32 and 33.

Figure 5:
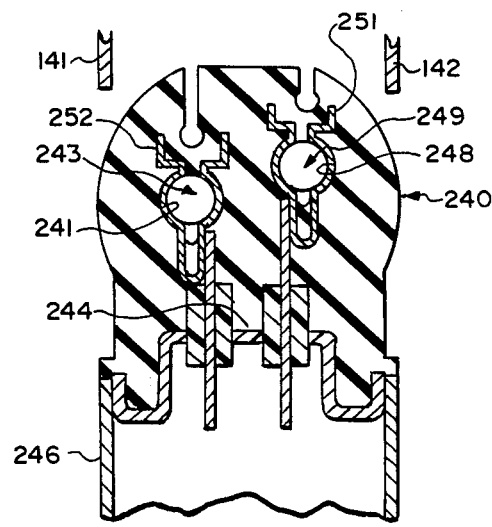
FIG. 5 is a vertical sectional view similar to the view shown in FIG. 4 and shows one of a plurality of electrical contacts mounted in the neck staggered above an electrical contact of another plurality of electrical contacts mounted in the neck.

In FIG. 5 is shown a modified embodiment of a pacer neck 240 constructed according to the teachings of the present invention and which has a shape similar to the shape of the neck 40 in FIG. 4 as shown. In this embodiment, a first lumen 241 in a main body portion 242 of the neck 240 has an axis 243 which extends longitudinally of the neck and generally parallel to a top side 244 of a metal pacer case 246.

A second lumen 248 also has an axis 249 that extends longitudinally of the pacer neck 240 and generally parallel to the top side of the pacer case 246 but above the axis 243 of the first lumen 241 so that the second lumen 248 is staggered above the first lumen 241. With this arrangement, contacts 251 in the second lumen 248 are staggered above contacts 252 in the first lumen 241 and can be positioned closer to each other thereby to minimize the width of the pacer neck 240.

The staggering can also be effected in a direction along the length of each lumen. In this respect, in FIG. 6 a contact 351 is shown in phantom in the first lumen 102 at a distance further inwardly from the outer end 108 of the snout portion 42 than is a contact 352 shown in phantom in the second lumen 104. In this way, the contacts of the first and second pluralities of contacts 90 and 100 are not adjacent each other but are staggered relative to each other along the length of the respective lumens 102 and 104 such that the lumens 102 and 104 can be closer together. This also enables the width of the neck 40 to be maintained at a minimum.

It will be appreciated that the pacer system 10 and particularly the pacer 12 of the present invention have a number of advantages, some of which have been described above and others of which are inherent in the invention.

Specifically, the soft, pliable elastomeric neck 40 molded about the contacts 91-93, 100 facilitates insulating of the contacts 91-93, 100, from each other. Additionally, the annular ribs 121-124 within the lumens 102 and 104 in the neck 40 provide moisture seals preventing electrolytic fluids from establishing a conductive path between an adjacent electrical contacts 91-93 or 100.

Furthermore, the simple construction of the neck 40 and the electrical contacts 91-93, 100 enables a plurality of electrical contacts 91-93, 100 to be mounted to the top side 44 of the metal case 46.

In the illustrated embodiment, three electrical contacts are shown. However, depending upon the size of the contacts 91-93, 100 and the number of contacts 91-93, 100 needed, six electrical contacts and perhaps up to ten electrical contacts can be mounted within the neck 40.

Also, the elongate snout portion 42 provides a strain relief function in preventing sharp bends in the proximal end portion 24 of the pacing lead 14.

Still further, the interference or tight fitting of the cap 140 over the main body portion 41 of the neck 40 facilitates a compressing of the electrical contacts 91-93, 100 about the ring electrodes 31, 32 and 33 on the proximal end portion 24 of the pacing lead 14, with the displaced material of the rounded sides of the main body portion 41 being moved into the space of the slots 161, 162 and lumens 102, 104, thereby to ensure good electrical contact throughout the useful life of the pacing system 10.

Also from the foregoing description, it will be apparent that modifications can be made to the cardiac pacing system 10 without departing from the teachings of the present invention. For example, for a pacer having a small narrow case, only one lumen is provided in the soft neck thereof. Accordingly, the scope of the invention is only to be limited as necessitated by the accompanying claims.

I claim:

1. A cardiac pacing system comprising: a cardiac pacer; and a pacing lead having a distal end and a proximal end having at least one ring electrode thereon; said pacer comprising a metal case mounting electronic-/electrical circuitry and a power supply therein and having a top side, a soft pliable elongate neck mounted to said top side of said case, connecting means inside said neck for connecting said cardiac pacer with said proximal end of said pacing lead, said connecting means comprising at least one generally U-shaped electrical contact, insulated conductor means extending through said top side for coupling said at least one electrical contact to electrical circuitry in said case, said neck having at least one elongate lumen therein into which extends said at least one electrical contact and which has an open end for receiving the proximal end of said pacing lead, and a hard elongate cap which is sized to fit over at least a portion of said neck containing said at least one electrical contact, which is releasably fixed over said neck, and which has a smaller width than the width of said neck so that after said proximal end of said lead is inserted into said lumen, fixing of said cap over said neck will compress said at least one electrical contact against said at least one ring electrode.

2. The system of claim 1 wherein said cap is made of hard plastic material.

3. The system of claim 1 wherein said cap is made of metal.

4. The system of claim 1 wherein said cap has two end edges and two side edges, and one of said end edges is hingedly connected to said top side of said metal case and the other end edge is snap fittingly coupled to said top side of said metal case.

5. The system of claim 1 wherein said neck is made of an elastomeric material.

6. The system of claim 1 wherein said neck is made of an elastomeric material which is molded onto the top side of said metal case and around said at least one electrical contact.

7. The system of claim 1 wherein said conductor means includes at least one conductor which extends through an insulated feedthrough mounted in said top side of said metal case and which is fixed, such as by welding, to said at least one electrical contact.

8. The system of claim 1 wherein said neck has a main body portion in which said at least one electrical contact is mounted and over which said cap is received, and a snout portion extending from one end of said main body portion, said at least one lumen extending through said snout portion, opening at an outer end of said snout portion, and having a closed end within said main body portion.

9. The system of claim 8 wherein said snout portion is positioned above a portion of said top side of said metal case.

10. The system of claim 8 wherein said snout portion has a flared end to form a bead around the outer end of said snout portion, said bead facilitating the tying of a suture around said snout portion adjacent said bead.

11. The system of claim 8 wherein said snout portion is generally oval in cross-section, and said neck has a second lumen parallel spaced from said first lumen and extending through said snout portion and into said main body portion, said second lumen having a closed end within said main body portion and an open end at the outer end of said snout portion.

12. The system of claim 11 wherein said snout portion has a flared end to form a bead around the outer end of said snout portion, said bead facilitating the tying of a suture around said snout portion adjacent said bead.

13. The system of claim 12 wherein said snout portion has an opening extending therethrough between said lumens, said opening facilitating the tying of a suture about the respective portions of said snout portion which are disposed between said opening and one side of said oval-in-cross-section snout portion around the respective first and second lumens.

14. The system of claim 1 wherein said connecting means comprises at least two of said electrical contacts.

15. The system of claim 14 wherein said lumen in said neck is generally cylindrical in cross-section and has on the cylindrical sidewalls thereof at least two annular ribs, one of which is located between the open end of said lumen and one of said electrical contacts, and the other of which is located between said two electrical contacts, said annular ribs forming sealing means for preventing fluids from communicating between said electrical contacts or for communicating from outside the pacer with the electrical contact closest to the open outer end of said lumen.

16. The system of claim 14 wherein said neck has a main body portion in which said at least one electrical contact is mounted and over which said cap is received, and a snout portion extending from one end of said main body portion, said snout portion is generally oval in cross-section, and said neck has a second lumen parallel spaced from said first lumen and extending through said snout portion and into said main body portion, said second lumen having a closed end within said main body portion and an open end at the outer end of said snout portion, and second connecting means comprising at least one generally U-shaped electrical contact are mounted in said neck and coupled via insulated conductor means extending through the top side of said metal case to electronic/electrical circuitry in said pacer case, said second named electrical contact being positioned partially in or extending into said second lumen.

17. The system of claim 14 wherein said neck has a second lumen parallel spaced from said first lumen and extending into said main body portion, said second lumen having a closed end within said main body portion and an open end, and having second connecting means comprising at least one generally U-shaped electrical contact and being mounted in said neck and coupled via insulated conductor means extending through the top side of said metal case to electronic/electrical circuitry in said pacer case, said second electrical contact being positioned partially in or extending into said second lumen.

18. The system of claim 17 wherein said first and second named connecting means include first and second pluralities of electrical contacts which are spaced apart along the length of said respective first and second lumens.

19. The system of claim 17 wherein said first and second pluralities of electrical contacts are spaced apart along the length of said respective first and second lumens and are positioned with the electrical contacts of the first plurality being offset along the length of said first and second lumens relative to said second plurality of contacts in said second lumen so that the contacts of the respective first and second pluralities of contacts are not adjacent each other and are staggered from each other along the length of the lumens.

20. The system of claim 17 wherein said first and second pluralities of electrical contacts are spaced apart along the length of said respective first and second lumens, said first lumen having an axis which extends generally parallel to the top side of said case and said second lumen having an axis which is also generally parallel to the top side of said case but which is located above the axis of said first lumen so that said electrical contacts in said second lumen are staggered above the electrical contacts in said first lumen, to allow the width of said neck to be kept to a minimum.

21. The system of claim 1 wherein said at least one electrical contact has spaced apart legs and said neck has a slot therein which extends along the elongate length of the neck at least in the portion of said neck above said lumen and said at least one electrical contact, said slot being adapted to receive an insertion tool or wedge for wedging said legs of said at least one electrical contact apart to facilitate insertion or withdrawal of said proximal end of said pacing lead into or out of the portion of said lumen containing said at least one electrical contact and to provide compressive space for the cover to close said legs of each contact around a lead ring electrode.

22. The system of claim 21 wherein said neck has a main body portion in which is mounted said at least one electrical contact, and said main body portion, in cross-section, has rounded sides extending from a top surface thereof to a narrower portion thereof with the displaced material of the rounded sides, when said cap is forced over and fixed over said main body portion, being moved into said lumen and said slot.

23. The system of claim 21 including a tool comprising an elongate bar and at least one elongate wedging rib extending from a side of said bar, said rib being received in said slot during assembly of said system to force the legs of said U-shaped contact apart to facilitate insertion of said lead into said lumen.

24. A method of connecting the proximal end of an implantable cardiac pacing lead to at least one electrical contact within a pacer neck of a cardiac pacer, said method comprising the steps of: providing at least one flexible electrical U-shaped spring contact having spaced apart legs on top of the metal case of a cardiac pacer; molding a soft, pliable elastomeric neck about said spring contact and simultaneously forming a lumen in said neck which is in communication with said spring contact, or has a portion of said spring contact disposed therein; inserting the proximal end portion of a pacing lead which has at least one ring electrode thereon into said lumen until the end thereof bottoms against the closed end of said lumen; constructing and arranging said ring electrode and said spring contact so that when said proximal end of said lead bottoms against said closed end of said lumen said ring electrode is in registry with and between said legs of said spring contact and causing said spring contact to be compressed against said ring electrode by fixing a hard cap, having an inside width less than the width of said neck, over said neck to said metal case.

25. The method of claim 24 including the steps of, providing a slot in the top of said elastomeric neck above said lumen and said spring contact; and, before inserting said pacing lead into said lumen, inserting a wedge into said slot to force the upper ends of said legs apart to facilitate insertion of said lead into said lumen.

* * * * *